United States Patent [19]

Baldwin et al.

[11] Patent Number: 4,929,637
[45] Date of Patent: May 29, 1990

[54] SUBSTITUTED THIOPHENE-2-SULFONAMIDE ANTIGLAUCOMA AGENTS

[75] Inventors: John J. Baldwin, Gwynedd Valley; Gerald S. Ponticello; Charles N. Habecker, both of Lansdale, all of Pa.

[73] Assignee: Merck & Co., Inc., Rahway, N.J.

[*] Notice: The portion of the term of this patent subsequent to Jan. 26, 2005 has been disclaimed.

[21] Appl. No.: 285,336

[22] Filed: Dec. 14, 1988

Related U.S. Application Data

[63] Continuation of Ser. No. 231,650, Aug. 10, 1988, abandoned, which is a continuation of Ser. No. 80,714, Jul. 31, 1987, abandoned, which is a continuation of Ser. No. 813,318, Dec. 24, 1985, abandoned.

[51] Int. Cl.$^5$ .............................................. A61K 31/38
[52] U.S. Cl. .................................... 514/445; 514/252; 514/256; 514/336
[58] Field of Search ........................... 549/60, 61, 66; 548/327; 546/184, 284, 347; 544/146, 379; 514/315, 326, 351, 396, 401, 408, 445

[56] References Cited

U.S. PATENT DOCUMENTS

| 4,386,098 | 5/1983 | Woltersdorf | 424/270 |
| 4,416,890 | 11/1983 | Woltersdorf | 424/270 |
| 4,426,388 | 1/1984 | Woltersdorf | 424/270 |
| 4,542,152 | 9/1985 | Shepard | 514/445 |
| 4,619,939 | 10/1986 | Maren | 514/363 |
| 4,721,794 | 1/1988 | Shepard | 549/65 |

FOREIGN PATENT DOCUMENTS

| 0182691 | 5/1986 | European Pat. Off. |
| 1459571 | 12/1976 | United Kingdom |
| 1468111 | 3/1977 | United Kingdom |

OTHER PUBLICATIONS

Kremlev, Chem. Abstr. 81, 120357r (1974).

*Primary Examiner*—Alan Siegel
*Attorney, Agent, or Firm*—William H. Nicholson; Joseph F. DiPrima

[57] ABSTRACT

Thiophene-2-sulfonamides with an alkyl or substituted-alkyl and an alkyl-S(O)$_n$-substituent are carbonic anhydrase inhibitors useful in the treatment of elevated intraocular pressure.

5 Claims, No Drawings

SUBSTITUTED THIOPHENE-2-SULFONAMIDE ANTIGLAUCOMA AGENTS

This is a continuation of co-pending application Ser. No. 231,650 filed on Aug. 10, 1988 now abandoned which is a continuation of application Ser. No. 080,714, filed Jul. 31, 1987 now abandoned, which is a continuation of application Ser. No. 813,318, filed Dec. 24, 1985 now abandoned.

SUMMARY OF THE INVENTION

This invention relates to novel thiophene-2-sulfonamides useful in the treatment of elevated intraocular pressure. More particularly this invention relates to compounds having the structural formula:

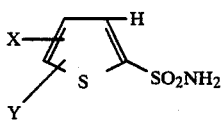

wherein X and Y are hereinafter defined, as well as the pharmaceutically and ophthalmologically acceptable salts thereof. This invention also relates to pharmaceutical compositions and the use thereof for systemic and ophthalmic use employing a novel compound of this invention as active ingredient for the treatment of elevated intraocular pressure, especially when accompanied by pathological damage such as in the disease known as glaucoma.

BACKGROUND OF THE INVENTION

Glaucoma is an ocular disorder associated with elevated intraocular pressures which are too high for normal function and may result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by many ophthalmologists to represent the earliest phase of glaucoma.

Many of the drugs formerly used to treat glaucoma proved not entirely satisfactory. Indeed, few advances were made in the treatment of glaucoma since pilocarpine and physostigmine were introduced. Only recently have clinicians noted that many $\beta$-adrenergic blocking agents are effective in reducing intraocular pressure. While many of these agents are effective in reducing intraocular pressure, they also have other characteristics, e.g. membrane stabilizing activity, that render them unacceptable for chronic ocular use. (S)-1-tert-Butylamino-[(4-morpholino-1,2,5-thiadiazol-3-yl)oxy]-2-propanol, a $\beta$-adrenergic blocking agent, was found to reduce intraocular pressure and to be devoid of many unwanted side effects associated with pilocarpine and, in addition, to possess advantages over many other $\beta$-adrenergic blocking agents, e.g. to be devoid of local anesthetic properties, to have a long duration of activity, and to display minimal tolerance.

Although pilocarpine, physostigmine and the $\beta$-blocking agents mentioned above reduce intraocular pressure, none of these drugs manifests its action by inhibiting the enzyme carbonic anhydrase and, thereby, impeding the contribution to aqueous humor formation made by the carbonic anhydrase pathway.

Agents referred to as carbonic anhydrase inhibitors, block or impede this inflow pathway by inhibiting the enzyme, carbonic anhydrase. While such carbonic anhydrase inhibitors are now used to treat intraocular pressure by oral, intravenous or other systemic routes, they thereby have the distinct disadvantage of inhibiting carbonic anhydrase throughout the entire body. Such a gross disruption of a basic enzyme system is justified only during an acute attack of alarmingly elevated intraocular pressure, or when no other agent is effective. Despite the desirability of directing the carbonic anhydrase inhibitor only to the desired ophthalmic target tissue, no topically effective carbonic anhydrase inhibitors are available for clinical use.

However, topically effective carbonic anhydrase inhibitors are reported in U.S. Pat. Nos. 4,386,098; 4,416,890; and 4,426,388. The compounds reported therein are 5 (and 6)-hydroxy-2-benzothiazolesulfonamides and acyl esters thereof.

To be an effective and acceptable topical agent, an ophthalmic carbonic anhydrase inhibitor must not only penetrate the ophthalmic tissues to reach the active sites within the eye, but it must also be devoid of those side effects including irritation, allergic reaction and the like which would militate against long term administration.

DETAILED DESCRIPTION OF THE INVENTION

The novel compounds of this invention have structural formula:

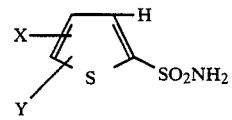

wherein:
X is
(1) —CN,
(2) halo such chloro, bromo or fluoro,
(3) R wherein R is $C_{1-5}$ alkyl, either straight or branched chain and either unsubstituted or substituted with one or more of:
  (i) —OH
  (ii)

wherein Rhu 1 and $R^2$ are independently hydrogen, $C_{1-5}$ alkyl, or $C_{2-5}$ alkanoyl,
  (iii) aryl, such as phenyl or naphthyl, either unsubstituted or substituted with one or more of —OH or $C_{1-3}$ alkyl, or
  (iv) a 6-membered nitrogen containing heteroaryl such as pyridyl, pyrazinyl, or pyrimidinyl;
(4)

or
(5)

wherein n is 0, 1 or 2.
Y is
(1) $C_{1-5}$ alkyl, either straight chain, branched chain or cyclic, and either unsubstituted or substituted with
   (a) hydroxy,
   (b) $C_{1-3}$ alkoxy,
   (c) methoxyethoxymethoxy,
   (d) amino,
   (e) mono- or di-($C_{1-5}$ alkyl)amino,
   (f) $C_{2-5}$ alkanoylamino;
   (g) aryl, such as phenyl or naphthyl, either unsubstituted or substituted with one or more of —OH or $C_{1-3}$ alkyl, or
   (h) a 6-membered nitrogen containing heteroaryl such as pyridyl, pyrazinyl, or pyrimidinyl;
(2)

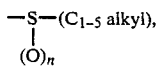

wherein the alkyl is either straight or branched or cyclic and either unsubstituted or substituted with items (a) through (h) as defined above;
(3) halo such as chloro, fluoro or bromo;
with the proviso that X and Y are not both halo.
It is preferred that X is

and that it be a 5-substituent. It is further preferred that R and Y are independently $C_{1-5}$ alkyl or substituted $C_{1-5}$ alkyl.

It is even more preferred that R is $C_{1-5}$ alkyl, hydroxy-$C_{1-5}$ alkyl, or mono- or di-($C_{1-5}$ alkyl)amino-$C_{1-5}$ alkyl, and that n is 0 or 2.

A novel process for preparing sulfides of this invention comprises treating a bromothiophene with an organometallic such as n-butyl lithium at about $-70°$ C. in an ethereal solvent such as ether, THF, glyme or the like for about 1 to 5 hours. This mixture is then added to a dialkyldisulfide in an inert atmosphere in an ethereal solvent at about $-25°$ to $-5°$ C. After about 15 minutes to 2 hours the mixture is then refluxed for about 1 to 4 hours. The starting reagents are as shown below:

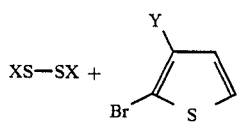

Functional groups on Y such as hydroxyl must be protected during the reaction for example as the methoxyethoxymethyl ether, which is readily removed after the reaction with a dilute mineral acid such as sulfuric acid at about 15° to 30° C. for about 0.5 to 3 hours.

The 4-alkylthio-5-substituted alkylthiophene-2-sulfonamides are prepared from known 3-alkylthiothiophene-2-carboxaldehyde. Treatment of the aldehyde with a Grignard reagent, LAH or the like yields the corresponding alcohol derivatives. Protection of the alcohol as the MEM ether or any other suitable protecting group such as THP, tert-butyldimethylsilyl or the like followed by the incorporation of the 2-sulfonamide group by chemistry described below provides the desired 4-alkylthio-5-substituted alkylthiophene-2-sulfonamides.

The 2-thio compounds may also be prepared by treating a 2-bromothiophene with a cuprous hydroxyalkyl mercaptide in refluxing quinoline for about 3-6 hours.

The methoxyethoxymethyl group may also be removed by treating the ether with dimethylboron bromide in chlorinated alkane such as methylene chloride at about $-78°$ C. for about 0.5 to 2 hours.

A novel process for preparing the sulfones of this invention comprises treating the sulfide with an oxidizing agent such as OXONE® ($2KHSO_5.K_2SO_4.KHSO_4$) (Dupont) followed by removal of any protecting group. It is often advisable to protect hydroxyl groups during the oxidation and it is readily accomplished by means of methoxyethoxymethyl ethers which can be removed by treatment with a mineral acid as described previously. The oxidation proceeds readily in aqueous alcohol at about 15° to 30° C. over a period of about 4 hours.

The novel sulfoxides of this invention are prepared by oxidation of the sulfides with sodium metaperiodate at about 15° to 25° C. in aqueous alcohol for about 8 to 36 hours.

Those compounds wherein the Y group carries an alkoxy group are prepared by treating the methoxyethoxymethyl ether in the appropriate alcohol with cold 50% (v/v) aqueous sulfuric acid for about 15 minutes to 1 hour at ambient temperature. The reaction is exemplified by the following:

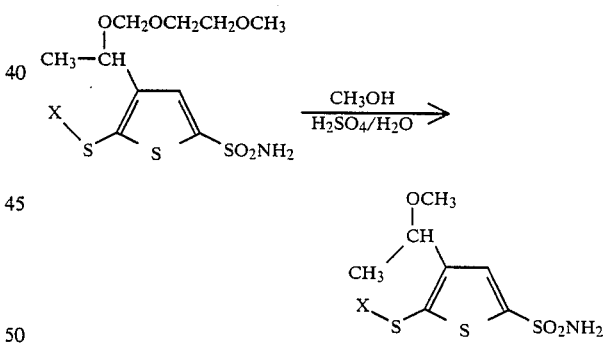

The sulfonamide group is introduced to the 2-position of the thiophene by treating the thiophene with an organometallic reagent such as n-butyl lithium in an ethereal solvent such as THF at $-78°$ C. for about 1-3 hours. The lithium thiophene solution is then exposed to sulfur dioxide gas for about 2 to 5 hours while warming to about $-40°$ C. The isolated lithium salt is then dissolved in sodium bicarbonate solution and treated with N-chlorosuccinimide. The resulting thiophene sulfonyl chloride in an inert solvent such as acetone is then added to concentrated ammonium hydroxide dropwise at about ice-bath temperature and the mixture is aged for about 0.5 to 2 hours.

Novel compounds wherein the Y group carries an amino substituent are prepared by treating the corresponding hydroxyl compound with sulfuric acid in an excess of acetonitrile at about 15° to 25° C. for about 18 to 36 hours (Ritter Reaction). The resulting acetylamino compound may be reduced with borane dimethylsulfide complex in an ethereal solvent at reflux temperature for about 0.5 to 3 hours.

Alternatively, the monoalkylamino derivative may be prepared by acid hydrolysis of the intermediate amide derived from the Ritter reaction followed by re-acylation with an alkanoyl chloride or anhydride to provide a new amide. Reduction of this amide with borane as described above yields the monoalkylamino derivative. The corresponding dialkylamino derivatives are prepared from the corresponding monoalkylamino derivative by acylation with an alkanoyl chloride or anhydride followed by reduction of the amide with diborane to provide the dialkylamino derivatives.

A process of preparing ketones as exemplified by 8 (Y=—CH$_3$, —CH$_2$OH, —CH(CH$_3$)OH) of the invention is described in Scheme I. Functional groups on Y such as hydroxy must be protected during the reaction sequence for example as the methoxyethoxymethyl ether. Bromination of 1 with NBS/CCl$_4$ provides the 2 bromothiophene 2. Treatment of 2 with n-butyl lithium followed by reaction with either dimethylformamide or dimethylacetamide yields the formyl or acetyl derivative 3, respectively. Reduction of 3 with chemical reducing agents such as LiAlH$_4$, NaBH$_4$ or the like yields the alcohol 4. In order to differentiate alcohols when another protected hydroxyl is present, the second alcohol moiety is protected as the tert-butyldimethylsilyl ether 5. Using previously described chemistry the sulfonamide group is next incorporated onto 5 to yield 6. The silyl group is removed by the use of F$^-$ to provide 7 and the alcohol 7 is oxidized by either MnO$_2$, Sarrett oxidation, a Jones oxidation, or the like to the ketone 8. In the examples where Y contains a hydroxyl group protected as a methoxyethoxymethyl ether, the group is removed by treatment with aqueous methanolic mineral acid. In cases where Y contains an amino group these compounds are prepared from the alcohol as previously described above (Ritter reaction).

5-Aralkylsulfone-4-alkylketonethiophene-2-sulfonamides are prepared from 2,3-dibromothiophene. Treatment with n-BuLi, LDA or the like provides the 2-lithiothiophene which is then treated with an aralkyldisulfide to provide the 2-aralkylsulfide-3-bromothiophene. Treatment with another equivalent of base, described above, yields the 3-lithio derivative which on reaction with DMF provides the 3-carboxaldehyde derivative. Manipulation of this structure as previously described provides the desired 5-aralkylsulfone-4-alkylketonethiophene-2-sulfonamides. By changing the order of reagents the corresponding 4-aralkylsulfone-5-alkylketonethiophene-2-sulfonamides may be prepared.

Scheme I

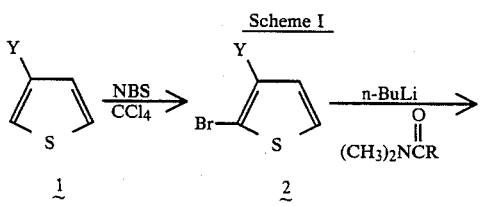

-continued
Scheme I

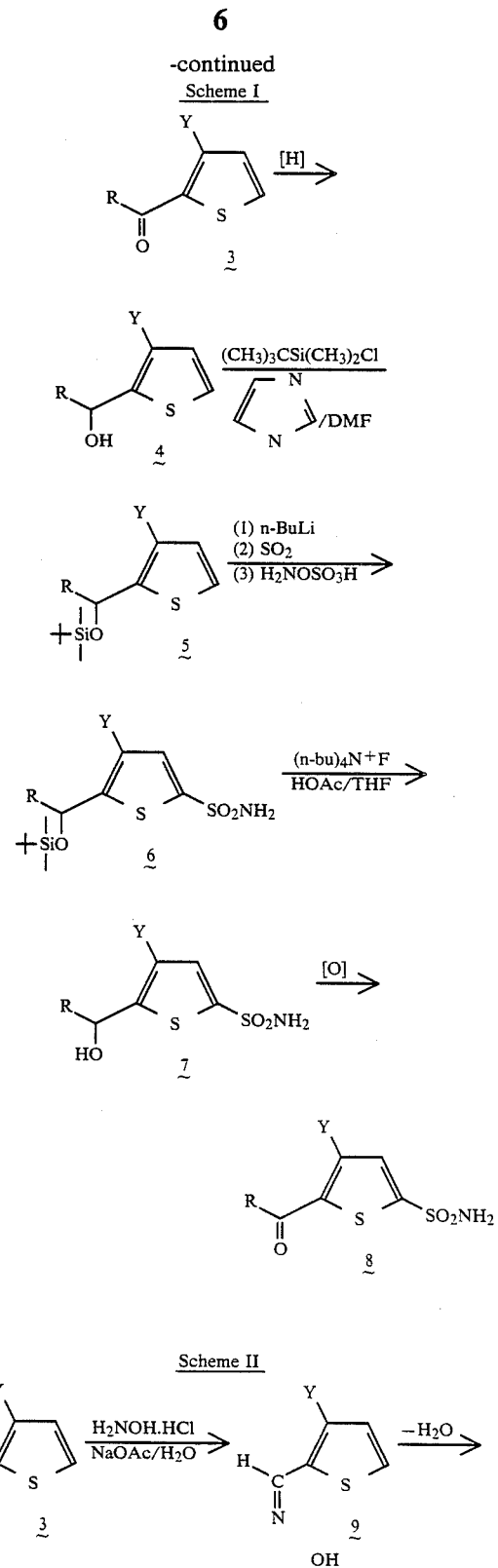

Scheme II

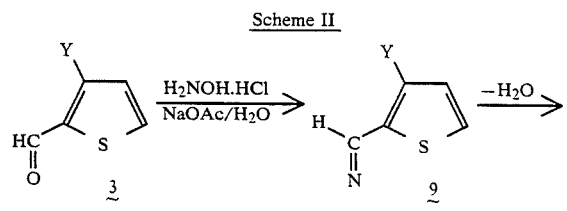

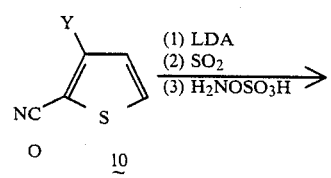

-continued
Scheme II

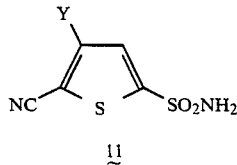

11

Those compounds wherein the X-group is —CN, are prepared from intermediate 2 (Scheme I). Treatment of aldehyde 3 with hydroxylamine yields the syn- and anti-oximes 9. Dehydration of 9 with acetic anhydride, thionyl chloride, DMF, trifluoroaceticanhydride or the like provides the nitrile 10. Treatment of 10 with lithium (diisopropyl)amide (LDA) followed by SO₂ and hydroxylamine-O-sulfonic acid yields the sulfonamide 11. Examples of Y containing hydroxyl and amino functions are prepared as previously described.

Treatment of 2 with LDA followed by SO₂ and hydroxylamine-O-sulfonic acid gives the corresponding 2-sulfonamide-5-bromothiophene derivative.

The novel pharmaceutical formulations of this invention include formulations for systemic administration and ophthalmic formulations designed for topical ocular administration, preferably the latter.

The formulations for systemic administration comprise a non-toxic pharmaceutically acceptable carrier and an effective amount of one or more of the novel compounds of this invention. They may be in a form (a) for oral administration; e.g., as tablets, in combination with other compounding ingredients customarily used such as talc, vegetable oils, polyols, benzyl alcohols, gums, gelatin, starches and other carriers; dissolved or dispersed or emulsified in a suitable liquid carrier; in hard or soft capsules, encapsulated in a suitable material; or (b) for parenteral administration; e.g., dissolved or dispersed in a suitable liquid carrier as a solution, suspension or emulsion, or (c) for transdermal application, e.g. as a patch.

The active drugs of this invention are most suitably administered in the form of ophthalmic pharmaceutical compositions adapted for topical administration to the eye such as a solution, suspension, gel, ointment, or as a solid insert. Formulations of these compounds may contain from 0.01 to 15% and especially 0.5% to 2% of medicament. They may contain a novel compound of this invention as the sole medicament or may contain as well an effective amount of a β-adrenergic blocking agent such as timolol maleate or a parasympathomimetic agent such as pilocarpine. The two active principles are present in approximately equal amounts on a weight basis.

The pharmaceutical preparation which contains the active compound may be conveniently admixed with a non-toxic pharmaceutical inorganic or organic carrier. Typical of pharmaceutically acceptable carriers are, for example, water, mixtures of water and water-miscible solvents such as lower alkanols or aralkanols, vegetable oils, polyalkylene glycols, petroleum based jelly, ethyl cellulose, ethyl oleate, carboxymethylcellulose, polyvinylpyrrolidone, isopropyl myristate and other conventionally employed acceptable carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, polyoxyethylene sorbitan monopalmitylate, dioctyl sodium sulfosuccinate, monothioglycerol, thiosorbitol, ethylenediamine tetraacetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like.

The pharmaceutical preparation may also be in the form of a solid insert such as one which after dispensing the drug remains essentially intact, or a bio-erodible insert that either is soluble in lacrimal fluids, or otherwise disintegrates.

Generally, doses of the present compounds of about 0.01 to about 50 mg/kg and preferably from about 0.1 to about 20 mg/kg of body weight per day may be used. Dosage may be single or multiple depending on the daily total required and the unit dosage.

EXAMPLE 1

4-(1-Hydroxypropyl)-5-methylsulfonylthiophene-2-sulfonamide

Step A: Preparation of
3-(1-Hydroxypropyl)-2-methylthiothiophene

To a stirred solution of ethylmagnesium bromide (60 ml, 0.12 mol of a 2.0M solution in THF) in ether (50 ml) was added dropwise under a nitrogen atmosphere 2-methylthiothiophene-3-carboxaldehyde (15.8 g, 0.10 mol) in ether (10 ml) over a ½ hour period at ice bath temperature. The mixture was stirred at room temperature for 2 hours. The mixture was cooled in an ice bath and the complexes were decomposed by adding NH₄Cl (10.6 g) in 100 ml of water. The aqueous layer was separated and was extracted with ether (2×50 ml). These extracts were combined with the ether layer and were washed with saturated NaCl solution, saturated NaHCO₃ solution and again with saturated NaCl solution. The ether solution was dried over anhydrous Na₂SO₄, filtered and concentrated in vacuo at room temperature to give 17.7 g of amber liquid (94%). TLC showed only minor impurities and NMR confirmed the structure.

Step B: Preparation of
3-[1-(Methoxyethoxymethoxy)propyl]-2-methylthiothiophene

To a stirred solution of 3-(1-hydroxypropyl)2-methylthiothiophene (17.7 g, 0.094 mol) in dry methylene chloride (100 ml) was added methoxyethoxymethyl chloride (20.6 g, 0.165 mol) followed by N,N,-diisopropylethylamine (21.3 g, 0.165 mol). The mixture was stirred at room temperature overnight. The mixture was washed with water, dried over anhydrous Na₂SO₄, filtered and concentrated in vacuo at room temperature to give 24.4 g of amber oil (94% yield). NMR confirmed the structure and mass spectral analysis confirmed the molecular weight at 276.09.

Step C: Preparation of 4-[1-(Methoxyethoxymethoxy)propyl]-5-methylthiothiophene-2-sulfonamide To a stirred solution of 3-[1-(methoxyethoxymethoxy)propyl]-2-methylthiothiophene (24.0, 0.087 mol) in dry THF (175 ml) cooled to −78° C. was added dropwise under nitrogen atmosphere n-butyl lithium (59.4 ml, 0.095 mol of a 1.6M hexane solution). The resulting deep red solution was stirred at about −70° C. for 2 hours and then SO$_2$ gas was introduced over the surface of the solution at −70 to −40° C. for 1 hour. The solution was stirred at about −40° C. for an additional 2 hours and was concentrated in vacuo to a viscous amber oil. The lithium salt was taken up in saturated NaHCO$_3$ solution (175 ml) and was stirred at ice bath temperature as N-chlorosuccinimide (17.7 g, 0.13 mol) was added portionwise over ½ hour. The mixture was stirred at ice bath temperature for 2 hours and then was extracted with chloroform (3×70 ml). The combined extracts were washed with water, dried, filtered and concentrated in vacuo to an amber liquid. The resulting sulfonyl chloride was taken up in acetone (50 ml) and was added dropwise to concentrated NH$_4$OH (100 ml) at ice bath temperature over ½ hour. The mixture was stirred for an additional hour at that temperature and the acetone was removed in vacuo. The oil which separated was extracted into ether (3×50 ml), washed with water and re-extracted with 0.5N KOH solution (3×100 ml). The combined KOH extracts were washed with ether, acidified with 6N HCl and again extracted into ether (2×100 ml). The combined ether extracts were washed with saturated solutions of NaCl and NaHCO$_3$ and again with saturated NaCl, dried over anhydrous Na$_2$SO$_4$, filtered and concentrated in vacuo at room temperature to give 24.3 g of amber liquid which was analytically pure (79%). NMR confirmed the structure and a molecular ion of M/Z 355 was observed in the mass spectrum.

Step D: Preparation of 4-[1-(Methoxyethoxymethoxy)propyl]-5-methylsulfonylthiophene-2-sulfonamide The 4-[1-(methoxyethoxymethoxy)propyl]-5-methylthiothiophene-2-sulfonamide (7.1 g, 0.02 mol) was dissolved in 50/50 ethanol/water (60 ml). To the stirred solution was added OXONE ® (18.4 g, 0.03 mol) and the mixture was stirred at room temperature for 4 hours. The acidic mixture was made slightly basic with sodium bicarbonate and the mixture was concentrated in vacuo to an oily solid residue. Extraction of this material with ethyl acetate (2×25 ml), washing with water, drying over anhydrous Na$_2$SO$_4$, filtering and concentration of the filtrate in vacuo gave a viscous yellow gum which contained minor impurities. The yield was essentially quantitative. NMR supported the structure and a molecular ion of M/Z 388 (M+H) was observed.

Step E: Preparation of 4-(1-Hydroxypropyl)-5-methylsulfonylthiophene-2-sulfonamide To a stirred solution of 4-[1-(methoxyethoxymethoxy)propyl]-5-methylsulfonylthiophene-2-sulfonamide (8.0 g, 0.02 mol) in methanol (20 ml) was added a cold solution of concentrated sulfuric acid (20 ml) in water (20 ml). The mixture was stirred at room temperature for 1 hour and the solution was basified with a slight excess of 40% NaOH and the suspension was filtered to remove precipitated salts. The filtrate was washed with ether and acidified with HCl. The acidified mixture was extracted with ethyl acetate (4×25 ml). The combined extracts were washed with saturated NaCl solution and dried over anhydrous Na$_2$SO$_4$. The solution was filtered and concentrated in vacuo at room temperature to give a viscous yellow oil which was a mixture of five components. Chromatography on 300 g of silica gel eluting with 5% methanol/CHCl$_3$ gave 3.0 g of a pure colorless oil. Trituration of the oil in n-butyl chloride gave a white solid (2.8 g) (45%). The product was recrystallized from 1,2-dichloroethane; m.p. 125.5–126.5° C.

Employing the procedures substantially as described in Example 1, but using as starting materials the alkylthiothiophenes and Grignard reagents described in Table I, there are produced the 4,5-disubstituted-thiophene-2-sulfonamides also described in Table I in accordance with the following reaction scheme:

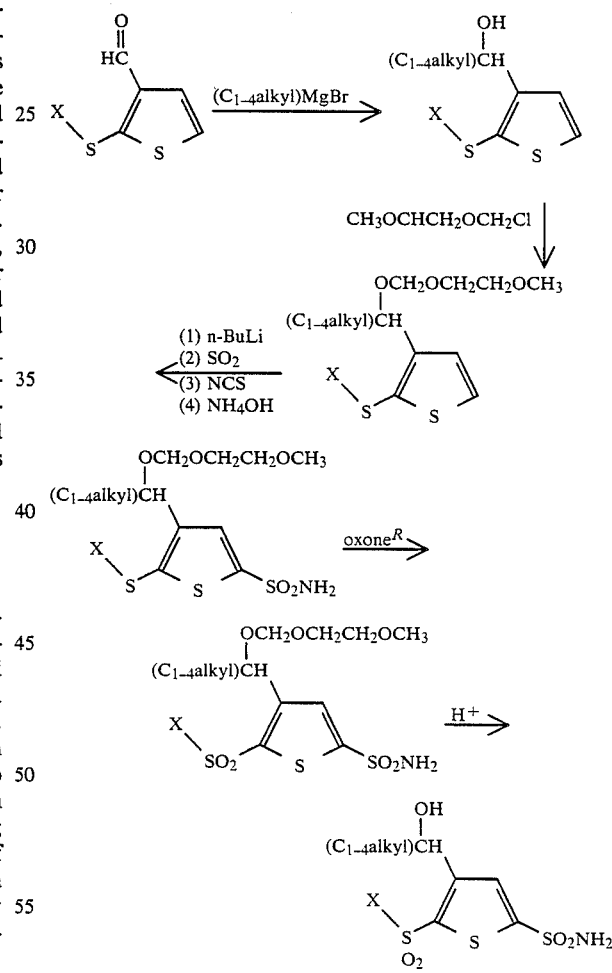

TABLE I

| R | OH<br>(C$_{1-4}$ alkyl)—CH— | m.p. (°C.) |
|---|---|---|
| —CH$_3$ | OH<br>\|<br>CH$_3$—CH— | 127–131 |
| —CH$_2$CH$_3$ | OH<br>\|<br>CH$_3$—CH— | 122–124 |

TABLE I-continued

| R | (C$_{1-4}$ alkyl)—CH(OH)— | m.p. (°C.) |
|---|---|---|
| —CH$_3$ | CH$_3$CH$_2$CH$_2$CH(OH)— | |
| —CH$_2$CH$_3$ | CH$_3$CH$_2$CH(OH)— | |
| —CH$_2$CH$_3$ | CH$_3$CH$_2$CH$_2$CH(OH)— | |
| —CH$_2$CH$_2$CH$_3$ | CH$_3$CH(OH)— | |
| —CH$_2$CH$_2$CH$_3$ | CH$_3$CH$_2$CH(OH)— | |
| —CH(CH$_3$)$_2$ | CH$_3$CH(OH)— | |
| —CH(CH$_3$)$_2$ | CH$_3$CH$_2$CH(OH)— | |
| —CH$_2$CH$_2$OH | CH$_3$—CH(OH)— | |
| —CH$_2$CH(OH)CH$_3$ | CH$_3$CH$_2$— | |
| —CH(OH)—CH$_3$ | CH$_3$CH$_2$— | |

EXAMPLE 2

4-(2-Hydroxyethyl)-5-methylsulfonylthiophene-2-sulfonamide

Step A: Preparation of 2-Bromo-3-(2-hydroxyethyl)thiophene

To a stirred solution of 2-(3-thienyl)ethanol (25.0 g, 0.195 mol) in carbon tetrachloride (250 ml) was added N-bromosuccinimide (34.7 g, 0.195 mol) in several portions over a 15 minute period. The mixture was stirred at room temperature for one hour. The succinimide was removed by filtration and the filtrate was concentrated in vacuo at room temperature to give the product as a viscous amber oil (40.2 g) (99%). TLC indicated that the product was pure and mass spectral analysis showed a molecular ion at M/Z 206. NMR supported the structure.

Step B: Preparation of 2-Bromo-3-[2-(methoxyethoxymethoxy)ethyl]thiophene

A solution of 2-bromo-3-(2-hydroxyethyl)thiophene (40.0 g, 0.193 mol) in methylene chloride (200 ml) was cooled in ice and methoxyethoxymethyl chloride (41.9 g, 0.336 mol) was added with stirring. After several minutes N,N-diisopropylethylamine (44.3 g, 0.336 mol) was added and the solution was stirred overnight at room temperature. The solvent was removed in vacuo and the residue was taken up in ether (150 ml) and water (75 ml). The ether layer was separated and was washed with saturated NaHCO$_3$ solution and with water, dried over anhydrous Na$_2$SO$_4$, filtered and concentrated in vacuo at room temperature to give 52.1 g of an amber liquid. TLC indicated that the product was pure and NMR confirmed the structure. Field desorption mass spectral analysis gave a molecular ion of M/Z 294. The yield was 91%.

Step C: Preparation of 3-[2-(Methoxyethoxymethoxy)ethyl]-2-methylthiothiophene To a stirred solution of 2-bromo-3-[2(methoxyethoxymethoxy)ethyl]thiophene (51.8 g, 0.175 mol) in anhydrous ether (125 ml) cooled to −70° C. was added n-butyl lithium (109.4 ml of a 1.6M solution in hexane, 0.175 mol) under a nitrogen atmosphere over a 1½ hour period. A tan suspension resulted which was stirred for an additional 1 hour and then was diluted with dry THF (100 ml) and was passed under nitrogen into a stirred solution of dimethyldisulfide (18.8 g, 0.20 mol) in anhydrous ether (50 ml) at −15° C. The resulting mixture was stirred at −15° C. for ½ hour and at reflux for 2 hours. The dark mixture was cooled to 0° C. and water (100 ml) was added carefully. The organic layer was separated and washed with saturated NaCl solution, dried over anhydrous Na$_2$SO$_4$, filtered and concentrated in vacuo at room temperature. The crude liquid (44.6 g) was distilled, the product being collected at 110–140° C. at 0.7 mm to give 34.6 g of pure product. Yield 75%. NMR supported the structure.

Step D: Preparation of 4-[2-(Methoxyethoxymethoxy)ethyl]-5-methylthiothiophene-2-sulfonamide To a stirred solution of 4-[2-(methoxyethoxymethoxy)ethyl]-5-methylthiothiophene (34.4 g, 0.13 mol) in THF (250 ml) cooled to −40° C. was added dropwise over ½ hour under nitrogen atmosphere n-butyl lithium (89.4 ml of a 1.6M solution in hexane, 0.143 mol). The resulting yellow solution was stirred at −40° C. for an additional one hour. Then anhydrous SO$_2$ was introduced over the surface of the solution for 1½ hour at about −20° C. The solution was concentrated in vacuo at room temperature to a viscous yellow oil. The oil was dissolved in saturated NaHCO$_3$ solution (200 ml) and N-chlorosuccinimide (24.4 g, 0.183 mol) was added portionwise over ½ hour at 5° C. Stirring was continued for an additional 2½ hours at 0° C. The oil which had separated was extracted into chloroform, washed with water and dried over anhydrous Na$_2$SO$_4$. Filtration and concentration of the filtrate in vacuo gave the sulfonyl chloride as an amber liquid. The liquid was dissolved in acetone (75 ml) and was added dropwise to concentrated NH$_4$OH (150 ml) over ½ hour with ice bath cooling. The acetone was removed in vacuo and the sulfonamide was extracted into chloroform. This solution was dried, filtered and concentrated in vacuo to give the crude sulfonamide as an oil. The sulfonamide was extracted into 0.5N KOH solution (300 ml). The basic solution was washed with ether, acidified with 6N HCl, and extracted with ether. The ether extract was washed with water, dried over anhydrous Na$_2$SO$_4$, filtered and concentrated in vacuo at room temperature to give 31.8 g (72%) of an amber oil. NMR supported the structure. Mass spectrum showed a molecular ion of M/Z 341.

Step E: Preparation of 4-[2-(Methoxyethoxymethoxy)ethyl]-5-methylsulfonylthiophene-2-sulfonamide The 4-[2-(methoxyethoxymethoxy)ethyl]-5-methylthiothiophene-2-sulfonamide (6.8 g, 0.02 mol) was dissolved in 50% aqueous ethanol (60 ml) and OXONE ® (18.4 g, 0.03 mol) was added. The mixture was stirred at room temperature for 3 hours, then basified with NaHCO$_3$, filtered, and concentrated in vacuo at room temperature to an oily solid residue. The residue was extracted with 50/50 ethyl acetate/chloroform. The extracts were dried over anhydrous Na$_2$SO$_4$, filtered and concentrated in vacuo to 6.6 g of colorless oil (88%). NMR supported the structure.

Step F: Preparation of 4-(2-Hydroxyethyl)-5-methylsulfonylthiophene-2-sulfonamide The 4-[2-(methoxyethoxymethoxy)ethyl]-5-methylsulfonylthiophene-2-sulfonamide (6.6 g, 0.0177 mol) was dissolved in methanol (25 ml) and was stirred at room temperature as cold 50% (v/v) sulfuric acid (40 ml) was added dropwise over 10 minutes. An additional quantity of methanol (25 ml) was added to dissolve the gum which separated and the solution was stirred for ½ hour. The solution was basified with sodium hydroxide and was washed with ether. The solution was acidified with HCl and was extracted with CHCl$_3$ and then with ethyl acetate. The ethyl acetate extract was washed with saturated NaCl solution, dried over anhydrous Na$_2$SO$_4$, filtered and concentrated in vacuo at room temperature to give 4.1 g of crude oil which was chromatographed on silica gel (100 g) eluting with 5% methanol in chloroform. There was recovered 2.5 g of white solid which provided 1.5 g of analytically pure, material, m.p. 120–124° C.

EXAMPLE 3

4-(1-Hydroxyethyl)-5-methylsulfinylthiophene-sulfonamide

Step A: Preparation of 4-[1-(Methoxyethoxymethoxy)ethyl]-5-methylsulfinylthiophene-sulfonamide To a stirred solution of 4-[1-(methoxyethoxymethoxy)ethyl]-5-methylthiothiophene-2-sulfonamide (6.8 g, 0.02 mol) in 50% aqueous ethanol (40 ml) was added sodium metaperiodate (4.8 g, 0.0224 mol). After several minutes solid began to separate. The mixture was stirred for 17 hours at room temperature. The suspension was filtered and the filtrate was concentrated to dryness in vacuo. The residual oily solid was chromatographed on silica gel (100 g) using 5% methanol in chloroform to give 6.68 g (94%) of pale yellow gum

Step B: Preparation of 4-(1-Hydroxyethyl)-5-methylsulfinYlthiophene-2-sulfonamide To a stirred solution of 4-[1-(methoxyethoxymethoxy)ethyl]-5-methylsulfonylthiophene-sulfonamide (6.58 g, 0.0186 mol) in methanol (25 ml) was added dropwise over a 10 minute period a cold solution of 50% (by volume) sulfuric acid. The solution was stirred for an additional 20 minutes at room temperature. The reaction solution was basified with NaHCO$_3$ with cooling and was concentrated to dryness in vacuo at 40° C. bath temperature. The solid residue was extracted with hot ethyl acetate and with 20% methanol/ethyl acetate.

Concentration of the extracts in vacuo gave 4.0 g of solid which was purified by chromatography on silica gel using 5% methanol in methylene chloride. There was obtained 3.0 g (60%) of product, m.p. 172–185° C.

EXAMPLE 4

4-(1-Methoxyethyl)-5-methylthiothiophene-2-sulfonamide

To a stirred solution of 4-[1-(methoxyethoxymethoxy)ethyl]-5-methylthiothiophene-2-sulfonamide (6.8 g, 0.02 mol) in methanol (25 ml) was added dropwise 50% (by volume) cold sulfuric acid (50 ml) over a 10 minute period. The solution was stirred for an additional ½ hour at room temperature and the mixture was basified with NaHCO$_3$ with cooling. The gum which separated was extracted into ethyl acetate. The aqueous layer was concentrated to dryness in vacuo and the solid residue was extracted with hot ethyl acetate. The ethyl acetate extracts were combined, dried over anhydrous Na$_2$SO$_4$, filtered and concentrated in vacuo to give an amber liquid which was purified by chromatography on silica gel (100 g) using ethyl acetate (40%)/hexane (60%). There was recovered 1.9 g (36%) of white solid, m.p. 86–94° C.

EXAMPLE 5

4-(1-Hydroxyethyl)-5-methylthiothiophene-2-sulfonamide

To boron tribromide (40 ml of a 1.0M solution in methylene chloride) cooled under a nitrogen atmosphere to −50° C. was added dropwise over ½ hour tetramethyl tin (7.15 g, 0.04 mol). The resulting solution was stirred for ½ hour at −50° C. and then for ½ hour at 15° C. The solution was cooled to −78° C. and 4-[1-(methoxyethoxymethoxy)ethyl]-5-methylthiothiophene-2-sulfonamide (3.41 g, 0.01 mol) in methylene chloride (15 ml) was added dropwise over 15 minutes. The mixture was stirred at −78° C. for ¾ hour and then poured into saturated NaHCO$_3$ solution. Some additional solid NaHCO$_3$ was added and the basic mixture was filtered. The filtrate was extracted with ethyl acetate (2×100 ml). The ethyl acetate solution was extracted with 0.5M KOH solution (2×100 ml). The KOH extracts were washed with ether and acidified with 6N HCl. The acidified mixture was extracted with ethyl acetate (2×50 ml). This extract was washed with saturated NaHCO$_3$, water, dried over anhydrous Na$_2$SO$_4$, filtered and concentrated in vacuo at ambient temperature. A pale amber oil was obtained (1.5 g). NMR confirmed the structure. After trituration in n-butyl chloride the oil solidified. Recrystallization from 1,2-dichloroethane gave 0.54 g (21%) of white solid, m.p. 100–102° C.

EXAMPLE 6

4-(1-Acetamidoethyl)-5-methylsulfonylthiophene-2-sulfonamide

To acetonitrile (30 ml) was added concentrated sulfuric acid (2.94 g, 0.03 mol) followed by 4-(1-hydroxyethyl)-5-methylsulfonylthiophene-2-sulfonamide (2.85 g, 0.01 mol). The resulting solution was stirred at room temperature for 24 hours. Only about ½ of the alcohol had reacted so additional sulfuric acid (2.94 g, 0.03 mol) was added. After another 16 hours at room temperature the reaction was complete. The mixture was basified with excess NaHCO$_3$. Acetonitrile (100 ml) was added, the mixture was filtered and the acetonitrile was evaporated in vacuo. The residue was taken up in ethyl acetate, washed with saturated NaCl solution, dried over anhydrous $Na_2SO_4$, filtered and concentrated in vacuo. The solid obtained was recrystallized from water to give 1.1 g (34%) of yellow solid, m.p. 114–117° C. HPLC and TLC confirmed the purity and NMR confirmed the structure.

EXAMPLE 7

4-[1-(Ethylamino)ethyl]-5-methylsulfonylthiophene-2-sulfonamide

To a stirred refluxing solution of 4-(1-acetamidoethyl)-5-methylsulfonylthiophene-2-sulfonamide (2.52 g, 0.0077 mol) in dry tetrahydrofuran (25 ml) under nitrogen atmosphere was added dropwise a solution of borane dimethylsulfide complex (2.3 ml, 0.023 mol) in THF (10 ml) over ½ hour. Reflux was continued for 1 hour. The solution was cooled in ice and acidified with 6N HCl (10 ml). The acidified solution was concentrated in vacuo. The residue was basified with saturated $NaHCO_3$ solution and was extracted with ethyl acetate. The product was extracted into 3N HCl. This was again basified with saturated $NaHCO_3$ solution, extracted with ethyl acetate, washed with saturated NaCl solution, dried over anhydrous $Na_2SO_4$, filtered and concentrated in vacuo. A white solid was obtained (1.33 g) (55%), m.p. 162.5–165° C. Recrystallization from ethyl acetate gave 1.23 g of product, m.p. 164–165.5° C. HPLC and TLC confirmed the purity and NMR confirmed the structure.

EXAMPLE 8

5-(2-Hydroxyethylsulfonyl)-4-methylthiophene-2-sulfonamide

Step A: Preparation of
2-(2-Hydroxyethylthio)-3-methylthiophene

A mixture of 2-bromo-3-methylthiophene (53.1 g, 0.30 mol), cuprous hydroxyethylmercaptide (46.4 g, 0.33 mol), pyridine (50 ml) and quinoline (200 ml) was stirred at reflux under nitrogen atmosphere for 4½ hours. The mixture was cooled, poured into 6N HCl and ice (800 ml), and repeatedly extracted with ether. The ether extract was washed with water, saturated $NaHCO_3$ solution and saturated NaCl solution and dried over anhydrous $Na_2SO_4$. The solution was filtered and concentrated in vacuo to obtain a brown liquid (41.9 g). Chromatography on silica gel gave 36.6 g of a pale yellow oil, (70%). TLC indicated that the product was pure. The structure was supported by NMR and mass spectrometry showed a molecular ion of M/Z=174.

Employing the procedures substantially as described in Example 1, Steps B, C, D and E there are produced in sequence starting with the product of Step A hereof:
Step B: 2-[2-(methoxyethoxymethoxy)ethylthio]-3-methylthiophene, as an oil in 98% yield;
Step C: 5-[2-(methoxyethoxymethoxy)ethylthio]-4-methylthiophene-2-sulfonamide, as an oil in 76% yield;
Step D: 5-[2-(methoxyethoxymethoxy)ethylsulfonyl]-4-methylthiophene-2-sulfonamide, as an oil in quantitative yield; and
Step E: 5-(2-hydroxyethylsulfonyl)-4-methylthiophene-2-sulfonamide, m.p. 144.5–148° C., in 29% yield.

EXAMPLE 9

4,5-Bis(ethylthio)thiophene-2-sulfonamide

To a stirred solution of 2,3-bis(ethylthio)thiophene (11.2 g, 0.055 mol) in dry tetrahydrofuran (100 ml) cooled to −78° C. under nitrogen atmosphere was added dropwise over ½ hour 1.55M n-butyl lithium in hexane (39 ml, 0.0605 mol). The resulting amber solution was stirred at about −75° C. for 1½ hours. Anhydrous sulfur dioxide gas was introduced over the surface of the solution over ½ hour at −75° to −20° C. The solution was stirred at −10° to −20° C. for 1½ hours. Concentration of the solution in vacuo gave the lithium salt as a pale yellow gum. The gum was dissolved in saturated $NaHCO_3$ solution (100 ml) and N-chlorosuccinimide (11.2 g, 0.0825 mol) was added portionwise over ½ hour at ice bath temperature. After 3 hours at ice bath temperature the mixture was extracted with chloroform. The extract was washed with water, dried over anhydrous $Na_2SO_4$, filtered and concentrated in vacuo to give the sulfonyl chloride as an amber oil. The sulfonyl chloride was dissolved in acetone (25 ml) and was added dropwise to concentrated $NH_4OH$ (100 ml) over ½ hour at ice bath temperature. After an additional hour at ice bath temperature the acetone was removed in vacuo and the oil which separated was extracted into ether. The product was extracted from the ether solution into 0.5N KOH solution. The KOH extract was acidified with excess 6N HCl and the oil was re-extracted into ether, washed with saturated $NaHCO_3$ solution and water. It was dried over anhydrous $Na_2SO_4$, filtered and concentrated in vacuo to a solid (8.1 g, 52%). Recrystallization from n-butyl chloride gave 5.74 g of white solid, m.p. 82–84° C.

EXAMPLE 10

4.5-Bis(ethylsulfonyl)thiophene-2-sulfonamide

The 4,5-bis(ethylthio)thiophene-2-sulfonamide (2.83 g, 0.01 mol) was dissolved in 50/50 ethanol/water (70 ml) and OXONE ® (18.4 g, 0.03 mol) was added. The mixture was stirred at room temperature for 72 hours. The suspension was filtered and the filtrate was basified with $NaHCO_3$ and was concentrated in vacuo to dryness. Both the solid residue obtained and the solids filtered from the reaction suspension were extracted with methanol. The solid obtained upon evaporation of the methanol was taken up in ethyl acetate, washed with water, dried over anhydrous $Na_2SO_4$ filtered and concentrated in vacuo at room temperature. White solid product was obtained (3.15 g) which contained some sulfoxide impurity. Recrystallizations from isopropanol and 50% aqueous methanol gave pure title compound (1.94 g, 56%), m.p. 175.5–177° C. HPLC and TLC confirmed the purity and NMR and mass spectrometry supported the structure.

EXAMPLE 11

5-(1-Hydroxyethyl)-4-methylsulfonyl-2-sulfonamide

Step A: Preparation of
2-(1-Hydroxyethyl)-3-methylthiothiophene

To a stirred solution of methylmagnesium bromide (51.7 g, 0.15 mol) in dry ether (50 ml) under nitrogen atmosphere was added dropwise 3-methylthiothiophene-2-carboxaldehyde (15.8 g, 0.10 mol) in dry ether (25 ml) at about 10° C. The solution was stirred at room temperature for 2¾ hours, cooled and decomposed by cautiously adding NH4Cl (16 g, 0.3 mol) in water (100 ml). The aqueous layer was separated and extracted with ether. The combined ether solution and extract were washed with saturated NaCl solution, dried over anhydrous Na2SO4, filtered and concentrated in vacuo at room temperature to a pale yellow oil which contained two components. Chromatography on silica gel gave pure product (13.5 g, 78%). NMR supported the structure.

Step B: Preparation of
2-[1-(Methoxyethoxymethoxy)ethyl]-3-methylthiothiophene

To a stirred solution of 2-(1-hydroxyethyl)3-methylthiothiophene (13.5 g, 0.077 mol) in dry methylene chloride (100 ml) was added methoxyethoxymethyl chloride (11.5 g, 0.092 mol) followed by N,N-diisopropylethylamine (12.1 g, 0.092 mol) with cooling. The solution was stirred at room temperature for 18 hours. Some starting material remained upon work up at this point. The material was recycled as above using ½ the above quantities of methoxyethoxymethyl chloride and N,N-diisopropylethyl amine. After 5 hours at room temperature the reaction was completed. The solution was washed with water, dilute HCl, saturated NaHCO3 solution and again with water. Then it was dried over anhydrous Na2SO4, filtered and concentrated in vacuo. Pure product was obtained as a yellow oil (17.6 g, 87%). TLC confirmed the purity and NMR and mass spectrometry (M/Z=262) supported the structure.

Step C: Preparation of
5-[1-(Methoxyethoxymethoxy)ethyl]-4-methylthiothiophene-2-sulfonamide To a stirred solution of 2-[1-(methoxyethoxymethoxy)ethyl]-3-methylthiothiophene (17.6 g, 0.067 mol) in dry THF (100 ml) under nitrogen atmosphere and cooled to −78° C. was added dropwise over 1 hour 1.55M n-butyl lithium (47.5 ml, 0.0737 mol) in hexane. The deep red solution was stirred at −78° C. for 1½ hours. Then anhydrous sulfur dioxide gas was introduced over the surface of the solution at −78° to −40° C. over 1 hour. Stirring at −40° C. was continued for 1½ hours and the solution was concentrated in vacuo to give the lithium salt as a yellow oil. The lithium salt was dissolved in saturated NaHCO3 solution, (100 ml) and N-chlorosuccinimide (13.6 g, 0.10 mol) was added portionwise over ½ hour with ice bath cooling. After stirring for an additional 3 hours at ice bath temperature the mixture was extracted with chloroform. The extract was washed with water, dried over anhydrous Na2SO4, filtered and concentrated in vacuo to obtain the sulfonyl chloride as a yellow oil. The sulfonyl chloride was taken up in acetone (50 ml) and was added dropwise to concentrated NH4OH (100 ml) at ice bath temperature over ½ hour. After another 1½ hours at ice bath temperature the acetone was removed in vacuo. The oil which separated was extracted into ether and then from the ether into 0.5N KOH. The KOH extract was acidified with excess 6N HCl and the product was re-extracted into ether. The ether extract was washed with saturated NaHCO3 solution, water, dried over anhydrous Na2SO4filtered and concentrated in vacuo. The product was obtained pure as an amber oil (14.6 g, 64%). NMR supported the structure and TLC confirmed the purity.

Step D: Preparation of
5-[1-(Methoxyethoxymethoxy)ethyl]-4-methylsulfonylthiophene-2-sulfonamide To a stirred solution of 5-[1-(methoxyethoxymethoxy)ethyl]-4-methylthiothiophene-2-sulfonamide (5.98 g, 0.0175 mol) in 50/50 ethanol/water (70 ml) was added OXONE ® (14.4 g, 0.0263 mol). The suspension was stirred at room temperature for 4½ hours. The mixture was basified with excess NaHCO3 and the entire mixture was concentrated to near dryness in vacuo. The residual moist solid was suspended in ethyl acetate and was filtered. The ethyl acetate extract was washed with water, dried over anhydrous Na2SO4, filtered and concentrated in vacuo to give a white solid, m.p. 93–102.5° C. (6.4 g, 98%). NMR supported the structure and TLC confirmed that the material was pure.

Step E: Preparation of
5-(1-Hydroxyethyl)-4-methylsulfonylthiophene-2-sulfonamide The 5-[1-(methoxyethoxymethoxy)ethyl]-4-methylsulfonylthiophene-2-sulfonamide (5.94 g, 0.0159 mol) was dissolved in 50/50 methanol/water (30 ml) with warming and concentrated sulfuric acid (15 ml) was added. The solution was cooled to ambient temperature and stirred for 1 hour. The methanol was removed in vacuo and the aqueous acid was diluted with water (50 ml). The product was extracted into ethyl acetate. The extract was washed with saturated NaHCO3 solution, water, dried over anhydrous Na2SO4, filtered and concentrated in vacuo. A colorless oil was obtained which solidified to a white solid. Several recrystallizations from water gave pure product (1.04 g, 23%), m.p. 121–127° C. NMR supported the structure and HPLC confirmed the purity.

EXAMPLE 13

5-Hydroxymethyl-4-methylsulfonylthiophene-2-sulfonamide

Step A: Preparation of
2-Hydroxymethyl-3-methylthiothiophene

To a stirred solution of 3-methylthiothiophene-2-carboxaldehyde (15.8 g, 0.10 mol) in ethanol (150 ml) cooled to 10° C. was added dropwise under nitrogen atmosphere a solution of sodium borohydride (3.78 g, 0.10 mol) in water (30 ml) and 1N KOH (5 ml) over ½ hour. The mixture was stirred at room temperature for 2 hours. The mixture was concentrated in vacuo at room temperature and the oily residue was taken up in chloroform (100 ml) and water (100 ml). The chloroform was separated and the aqueous layer was extracted with chloroform (50 ml). The combined chloroform extracts were washed with saturated NaCl, dried over anhydrous Na2SO4, filtered and concentrated in vacuo at room temperature to give a pale yellow liquid (14.2 g) which contained two components. Chromatography on silica gel gave 9.5 g (59%) of the title compound as a colorless oil. NMR supported the structure and mass spectral analysis by low resolution showed a molecular ion of M/Z=160.

Employing the procedures substantially as described in Example 12, Steps B through E, there was produced in sequence starting with the product from Step A hereof:

Step B: 2-(Methoxyethoxymethoxymethyl)-3-methylthiothiophene as a yellow liquid in 95% yield;

Step C: 5-(Methoxyethoxymethoxymethyl)-4-methylthiothiophene-2-sulfonamide as an oil in 64% yield;

Step D: 5-(Methoxyethoxymethoxymethyl)-4-methylsulfonylthiophene-2-sulfonamide in 95% yield, m.p. 104–107° C.; and Step E: 5-Hydroxymethyl-4-methylsulfonylthiophene-2-sulfonamide in 72% yield, m.p. 175–177.5° C.

EXAMPLE 14

5-Bromo-4-(l-hydroxyethyl)thiophene-2-sulfonamide

Step A: Preparation of 2-Bromo-3-(l-hydroxyethyl)thiophene

To a stirred solution of 3-(1-hydroxyethyl)thiophene (61.4 g, 0.48 mol) in carbon tetrachloride (550 ml) was added N-bromosuccinimide (89.4 g, 0.504 mol) portionwise over 1½ hours at 40° C. Stirring was continued for an additional 2 hours at ambient temperature. The reaction mixture was filtered and the filtrate was washed with water, saturated $NaHCO_3$ and again with water. The solution was dried over anhydrous $Na_2SO_4$ filtered and concentrated in vacuo at room temperature. This procedure gave 95.5 g (96%) of pale yellow oil. NMR supported the structure.

Step B: Preparation of 2-Bromo-3-[l-(methoxyethoxymethoxy)ethyl]thiophene

A solution of 2-bromo-3-(l-hydroxyethyl)thiophene (97.5 g, 0.47 mol) in dry methylene chloride (400 ml) was cooled in ice and N,N-diisopropylethylamine (68.2 g, 0.517 mol) was added followed by methoxyethoxymethYl chloride (64.4 g, 0.517 mol). The solution was stirred at room temperature over night. The dark solution was washed with water, 3N HCl, saturated $NaHCO_3$ and finally with water. The solution was dried over anhydrous $Na_2SO_4$ filtered and concentrated in vacuo at room temperature. A dark amber oil was obtained (123.1 g). The impure product was distilled and the product was collected at 108–116° C. at 0.7 mm Hg. to give 91.1 g (66%) of colorless liquid. NMR supported the structure.

Step C: Preparation of 5-Bromo-4-[l-(methoxyethoxymethoxy)ethyl]thiophene-2-sulfonamide To a stirred solution of dry diisopropylamine (12.6 g, 0.125 mol) in dry THF (100 ml) cooled to −5° C. under nitrogen atmosphere n-butyl lithium (66.7 ml of a 1.55 M hexane solution, 0.105 mol) was added dropwise over ½ hour. The solution was stirred for 1½ hours at −5° C. The resulting lithium diisopropylamide solution was added dropwise over 1 hour at below −70° C. to a stirred solution of 2-bromo-3-[l-(methoxyethoxymethoxy)ethyl]thiophene (29.5 g, 0.10 mol) in dry THF (50 ml). The solution was stirred at −70° C. for ½ hour and then at −70° to −50° C. for ½ hour. Recooled to −70° C. and anhydrous sulfur dioxide was introduced over the surface of the solution until the mixture became acidic. Stirring was continued at −40° to −60° C. for 1 hour and then the mixture was concentrated in vacuo at room temperature to give the lithio salt as a brown gum. The gum was dissolved in water (200 ml) containing sodium acetate (18.0 g, 0.22 mol) and the solution was cooled in an ice bath. Hydroxylamine-O-sulfonic acid (22.6 g, 0.20 mol) was added. The mixture was slightly acidic so another portion of sodium acetate (18.0 g, 0.22 mol) was added. The nearly neutral solution was stirred at room temperature over night. The mixture was extracted with chloroform (200 ml in 3 portions) and the sulfonamide was extracted into 0.5N KOH (200 ml). The KOH extract was washed with ether, acidified with excess 6N HCl and re-extracted into ether (300 ml). The ether extract was washed with saturated $NaHCO_3$ and water, dried over anhydrous $Na_2SO_4$ filtered and concentrated in vacuo to give 26.0 g (69%) of a viscous oil which solidified to a waxy solid. NMR supported the structure.

Step D: Preparation of 5-Bromo-4-(l-hydroxyethyl)thiophene-2-sulfonamide

5-Bromo-4-[l-(methoxyethoxymethoxy)ethyl]thiophene-2-sulfonamide (5.3 g, 0.014 mol) was dissolved in methanol (25 ml) and water (25 ml) was added. Some oil separated. To this stirred mixture was added sulfuric acid (25 ml) dropwise with cooling over 20 minutes. The resulting solution was stirred at room temperature over night. The methanol was removed in vacuo and the residual suspension was diluted with two volumes of water. The product was extracted into ethyl acetate. The extract was washed with saturated $NaHCO_3$, water, dried over anhydrous $Na_2SO_4$, filtered and concentrated in vacuo. This gave 4.0 g of a viscous amber oil. The crude oil was chromatographed on silica gel (150 ml) eluting with 5% methanol/chloroform to give 1.96 g of colorless oil which showed a single spot by TLC. Trituration of the oil in n-butyl chloride gave a white solid (1.69 g, 49%), m.p. 126–128.5° C. NMR supported the structure.

EXAMPLE 15

4-(1-(ethylamino)ethyl)-5-ethylsulfonylthiophene-2-sulfonamide

Step A: Preparation of 4-(1-Acetamidoethyl)-5-ethylsulfonylthiophene-2-sulfonamide To acetonitrile (40 ml) was added concentrated sulfuric acid (8.1 g, 0.0828 mol). Then 5-ethylsulfonyl-4-(1-hydroxyethyl)thiophene-2-sulfonamide (4.14 g, 0.0138 mol) was added and the solution was stirred at room temperature until no starting material remained (48 hours). The solution was neutralized by adding solid $NaHCO_3$ along with water (5 ml). The mixture was filtered and the solids were washed with acetonitrile. The filtrate and washings were concentrated in vacuo to an oil. This residual oil was taken up in ethyl acetate (125 ml). The extract was washed with saturated NaCl, dried over anhydrous $Na_2SO_4$, filtered and concentrated in vacuo at room temperature, to give 2.74 g (58%) of white solid which was a single product by TLC, m.p. 213–220° C. NMR supported the structure.

Step B: Preparation of 4-[1-(Ethylamino)ethyl]-5-ethylsulfonylthiophene-2-sulfonamide To a stirred, refluxing suspension of 4-(1-acetamidoethyl)-5-ethylsulfonylthiophene-2-sulfonamide (2.61 g, 0.0077 mol) in dry tetrahydrofuran under nitrogen atmosphere was added dropwise over ½ hour a solution of dimethylsulfide borane complex (2.3 ml of a 10 M solution, 0.023 mol) in dry THF (10 ml). The cloudy solution which formed was stirred at reflux for 1½ hours. The mixture was cooled in ice and acidified by the dropwise addition of 6N HCl (10 ml), and concentrated in vacuo at room temperature. The moist solid residue was basified with saturated NaHCO₃ and was extracted with ethyl acetate (4×50 ml). The amino product was extracted into 3N HCl (4×25 ml). The combined HCl extracts were neutralized with NaHCO₃ and extracted with ethyl acetate (4×50 ml). The ethyl acetate extract was dried over anhydrous Na₂SO₄, filtered and concentrated in vacuo at room temperature. A colorless oil was obtained which solidified to a white solid upon trituration in ethyl acetate. The crude yield was 1.99 g or 80%. The solid after recrystallization from ethyl acetate had m.p. 135–137.5° C. NMR supported the structure and HPLC confirmed the purity.

EXAMPLE 16

| | | |
|---|---|---|
| 4-(1-Hydroxyethyl)-5-ethyl-sulfonylthiophene-2-sulfonamide | 1 mg. | 15 mg. |
| Monobasic sodium phosphate .2H₂O | 9.38 mg. | 6.10 mg. |
| Dibasic sodium phosphate .12H₂O | 28.48 mg. | 16.80 mg. |
| Benzalkonium chloride | 0.10 mg. | 0.10 mg. |
| Water for injection q.s. ad. | 1.0 ml. | 1.0 ml. |

The title Compound, phosphate buffer salts, and benzalkonium chloride are added to and dissolved in water. The pH of the composition is adjusted to 6.8 and diluted to volume. The composition is rendered sterile by ionizing radiation.

EXAMPLE 17

| | |
|---|---|
| 4-(1-Hydroxypropyl)-5-ethyl-sulfonylthiophene-2-sulfonamide | 5 mg. |
| petrolatum q.s. ad. | 1 gram |

The title compound and the petrolatum are aseptically combined.

EXAMPLE 18

| | |
|---|---|
| 4-(1-Hydroxyethyl)-5-ethylsulfonyl-thiophene-2-sulfonamide | 1 mg. |
| Hydroxypropylcellulose q.s. | 12 mg. |

Ophthalmic inserts are manufactured from compression molded films which are prepared on a Carver Press by subjecting the powdered mixture of the above ingredients to a compressional force of 12,000 lbs. (gauge) at 300° F. for one to four minutes. The film is cooled under pressure by having cold water circulate in the platen. Ophthalmic inserts are then individually cut from the film with a rod-shaped punch. Each insert is placed into a vial, which is then placed in a humidity cabinet (88% R.H. at 30° C.) for two to four days. After removal from the humidity cabinet, the vials are stopped and then capped. The vials containing the hydrate insert are then autoclaved at 250° F. for ½ hour.

EXAMPLE 19

| | |
|---|---|
| 4-(2-Hydroxyethyl)-5-methylsulfonyl-thiophene-2-sulfonamide | 1 mg. |
| Hydroxypropyl cellulose q.s. ad. | 12 mg. |

Ophthalmic inserts are manufactured from a solvent cast film prepared by making a viscous solution of the powdered ingredients listed above using methanol as the solvent. The solution is placed on a Teflon plate and allowed to dry at ambient conditions. After drying, the film is placed in an 88% R. H. cabinet until it is pliable. Appropriately sized inserts are cut from the film.

EXAMPLE 20

| | |
|---|---|
| 4-[1-(Ethylamino)ethyl]-5-methyl-sulfonylthiophene-2-sulfonamide | 1 mg. |
| Hydroxypropylmethyl cellulose q.s. ad. | 12 mg. |

Ophthalmic inserts are manufactured from a solvent cast film which is prepared by making a viscous solution of the powdered blend of the above ingredients using a methanol/water solvent system (10 ml. methanol is added to 2.5 g. of the powdered blend, to which 11 ml. of water (in three divided portions) is added. The solution is placed on a Teflon plate and allowed to dry at ambient conditions. After drying, the film is placed in an 88% R. H. cabinet until it is pliable. Appropriately sized inserts are then cut from the film.

EXAMPLE 21

| | |
|---|---|
| 5-(2-Hydroxyethylsulfonyl)-4-methyl-thiophene-2-sulfonamide | 1 mg. |
| Hydroxypropylmethyl cellulose q.s. ad. | 12 mg. |

Ophthalmic inserts are manufactured from compression molded films which are prepared on a Carver Press by subjecting the powdered mixture of the above ingredients to a compressional force of 12,000 lbs. (gauge) at 350° F. for one minute. The film is cooled under pressure by having cold water circulate in the platen. Ophthalmic inserts are then individually cut from the film with a punch. Each insert is placed into a vial, which is then placed in a humidity cabinet (88% R. H. at 30° C.) for two to four days. After removal from the humidity cabinet, the vials are stopped and then capped. The vials containing the hydrated insert are then autoclaved at 250° F. for one-half hour.

It is highly preferred that the solid inserts of this invention are available for use by the patient in a pathogen free condition. Thus, it is preferred to sterilize the inserts and to insure against recontamination, the sterilization is preferably conducted after packaging. The best mode of sterilizing is to employ ionizing radiation including radiation emanating from Cobalt 60 or high energy electron beams.

What is claimed is:

1. A method of treating elevated intraocular pressure which comprises the administration to a patient in need of such treatment of an effective intraocular pressure-lowering amount of a compound of structural formula:

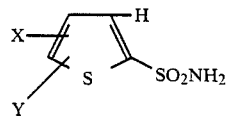

wherein:
X is (1) R wherein R is $C_{1-5}$alkyl, either straight or branched chain and either unsubstituted or substituted with one or more of:
(i) —OH
(ii)

wherein $R^1$ and $R^2$ are independently hydrogen, $C_{1-5}$alkyl or $C_{2-5}$alkanoyl,
(iii) phenyl or naphthyl, either unsubstituted or substituted with one or more of —OH, or $C_{1-3}$alkyl, or
(iv) a 6-membered nitrogen-containing heteroaryl selected from pyridyl, pyrazinyl or pyrimidinyl; or
(2)

wherein n is 0, 1 or 2;
Y
(1) $C_{1-5}$alkyl, either straight chain, branched chain or cyclic, and substituted with
(a) hydroxy,
(b) $C_{1-3}$alkoxy,
(c) methoxyethoxymethoxy,
(d) amino,
(e) $C_{1-5}$alkylamino,
(f) $C_{2-5}$alkanoylamino,
(g) phenyl or naphthyl, either unsubstituted or substituted with one or more of —OH or $C_{1-3}$alkyl, or (h) a 6-membered nitrogen containing heteroaryl selected from pyridyl, pyrazinyl, and pyrimidinyl; or
(2)

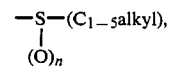

where the alkyl is either straight, branched or cyclic, and either unsubstituted or substituted with items (a) through (h) as defined above.

2. The method of claim 1 wherein the compound has structural formula:

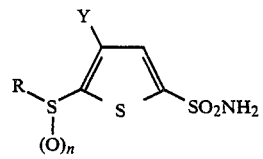

3. The method of claim 1 wherein R and Y are $C_{1-5}$alkyl and substituted $C_{1-5}$alkyl respectively.

4. The method of claim 3, wherein R is $C_{1-5}$ alkyl, hydroxy-$C_{1-5}$ alkyl or mono- or di-($C_{1-5}$ alkyl)amino-$C_{1-5}$ alkyl, and n is 0 or 2.

5. The method of claim 4 wherein the compound is:
4-(1-hydroxyethyl)-5-methylsulfonylthiophene-2-sulfonamide;
4-(1-hydroxypropyl)-5-methylsulfonylthiophene-2-sulfonamide;
4-(1-hydroxyethyl)-5-ethylsulfonylthiophene-2-sulfonamide;
4-(2-hydroxyethyl)-5-methylsulfonylthiophene-2-sulfonamide;
4-hydroxymethyl-5-ethylsulfonylthiophene-2-sulfonamide;
5-(2-hydroxyethylsulfonyl)-4-methylthiophene-2-sulfonamide; and
4,5-bis(ethylsulfonyl)thiophene-2-sulfonamide.

* * * * *